United States Patent [19]

Farnham

[11] Patent Number: 5,171,893
[45] Date of Patent: Dec. 15, 1992

[54] PROCESS FOR PRODUCING FLUORINATED ORGANIC COMPOUNDS

[75] Inventor: William B. Farnham, Wilmington, Del.

[73] Assignee: E. I. Du Pont de Nemours and Company, Wilmington, Del.

[21] Appl. No.: 801,344

[22] Filed: Dec. 2, 1991

Related U.S. Application Data

[62] Division of Ser. No. 424,470, Oct. 20, 1989, Pat. No. 5,093,512.

[51] Int. Cl.$^5$ .................... C07C 45/30; C07D 211/06
[52] U.S. Cl. ................................ 568/316; 568/348; 546/345
[58] Field of Search ................ 568/316, 348; 546/345

[56] References Cited

U.S. PATENT DOCUMENTS 4,634,787  1/1987  Wang .................................. 556/470
4,804,774  2/1989  Stahly ................................. 556/436

OTHER PUBLICATIONS

G. K. Prakash, et al., *J. Am. Chem. Soc.*, vol. III, 393–395 (1989).
J. D. Citron, *J. Organometal. Chem.*, vol. 30, 21–26 (1971).
G. P. Stahly and D. R. Bell, *J. Org. Chem.*, vol. 54, 2873–2877 (1989).

*Primary Examiner*—Mary C. Lee
*Assistant Examiner*—Joseph K. McKane

[57] ABSTRACT

This invention concerns a process for preparing fluoroalkyl substituted olefins, fluorinated ketones and fluorinated aromatic compounds by the catalyzed reaction of fluoroalkylsilanes with selected fluorinated olefins, acyl fluorides and fluorinated aromatic compounds, respectively.

31 Claims, No Drawings

PROCESS FOR PRODUCING FLUORINATED ORGANIC COMPOUNDS

This is a division of application Ser. No. 07/424,470, filed Oct. 20, 1989, U.S. Pat. No. 5,093,512.

BACKGROUND

1. Field of the Invention

This invention concerns the production of fluoralkyl substituted olefins, fluorinated ketones and fluorinated benzenes by the catalyzed reaction of fluoroalkylsilanes with selected fluorinated olefins, acyl fluorides, and fluorinated aromatic compounds, respectively. The products are useful as chemical intermediates, solvents and as monomers for polymerization.

2. Background Art

G. K. Prakash, et a., *J. Am. Chem. Soc.*, Vol. 111, 393–395 (1989) describe the reaction of the fluoride ion catalyzed reaction of trifluoromethyltrimethylsilane with ketones and aldehydes to give the corresponding α-trifluoromethyl substituted alcohol and trimethylfluorosilane. In a typical reaction, cyclohexanone was reacted with trifluoromethyltrimethylsilane in tetrahydrofuran in the presence of tetrabutylammonium fluoride at 0° C. After 1 hour, the solution was mixed with 0.5N HCl to hydrolyze the intermediate silyl ether, and then the product was isolated by distillation. In this case, a 77% yield of 1-trifluoromethylcyclohexanol is reported.

J. D. Citron, *J. Organometal, Chem.*, Vol. 30, 21–26 (1971) reports the uncatalyzed reaction of silicon compounds containing a variety of functional groups with acyl fluorides. Fluoroalkylsilanes are not mentioned as a reactant.

G. P. Stahly, U.S. Pat. No. 4,804,774, describes the reaction of quinones with perfluoroalkylsilanes in the presence of certain phosphorous containing catalysts to form compounds wherein the silicon atom is attached to one of the oxygen atoms of the quinone and the perfluoroalkyl group is attached to the carbon atom to which said oxygen is attached. In other words, the perfluoroalkylsilane adds across the carbonyl double bond. In Comparative Examples A and B, this reference describes the reaction of benzoquinone with triethyltrifluoromethylsilane, catalyzed by sodium fluoride and calcium fluoride respectively. It is reported that no reaction takes place.

U.S. Pat. No. 4,634,787 to Wang claims the fluoride catalyzed reactions of trihalomethylsilanes with aldehydes, ketones and quinones. The products are (2,2,2-trihalo-1,1-dihydrocarbylethoxy)trihydrocarbylsilanes. Preferred halo groups are chloro and bromo. Fluoro groups are neither exemplified nor specifically mentioned.

G. P. Stahly and D. R. Bell, *J. Org. Chem.*, Vol. 54, 2873–2877 (1989) report the catalyzed reactions of quinones with trifluoromethylsilyl compounds, wherein the silyl compound adds across the carbonyl of the quinone. Thus, the reaction of 1,4-benzoquinone with trifluoromethyltrimethylsilane yields 4-trifluoromethyl-4-trimethylsiloxy-2,5-cyclohexadieneone. Some of the catalysts are cesium fluoride, potassium bifluoride, tetrabutyl ammonium bifluoride, potassium cyanide and potassium carbonate.

SUMMARY OF THE INVENTION

A process for the production of fluoroalkyl substituted olefins, fluorinated ketones and fluorinated aromatic compounds comprising contacting fluoroalkylsilanes of the formula:

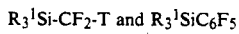

wherein:
each $R^1$ is independently selected from hydrocarbyl or hydrocarbyl containing inert substituents; and
T is fluorine, or

wherein:
each W is independently selected from hydrocarbyl, hydrocarbyl containing inert substituents and/or reactive silyl radicals, hydrogen and fluorine, with fluorinated olefins, acyl fluorides and fluorinated aromatic compounds of the formulas

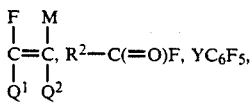

and perfluoropyridine, wherein:
$Q^1$ and $Q^2$ are independently selected from fluorine and $-CFX_2$;
M is $-CFX_2$ and $-OCFX_2$;
each X is independently selected from fluorine, chlorine, hydrogen, hydrocarbyl and hydrocarbyl containing inert substituents and/or reactive vinyl radicals and a covalent bond, provided that each X may be such that the groups $Q^1$ and $Q^2$ are part of a carbocyclic or heterocyclic ring which includes the reactive fluorinated olefin;
$R^2$ is hydrocarbyl or hydrocarbyl containing inert substituents and/or acyl fluoride radicals; and
Y is a nonreactive group whose Hammett sigma constant is about +0.5 or more; in the presence of a GTP catalyst or a catalyst that is a source of fluoride or bifluoride anions and in the presence of a solvent. The fluorinated organic compounds that are produced by such a process are useful as chemical intermediates, monomers and solvents. Polymers useful for molding or for low molecular weight solvent resistant caulks are also produced by this process.

DESCRIPTION OF THE INVENTION

The present process utilizes a silicon compound containing a fluoroalkyl group that, in effect, is exchanged for a fluorine atom in selected organic molecules. Thus, when reacting a fluoroalkylsilane with a fluorinated olefin, the fluoroalkyl group from the silane replaces one of the vinylic fluorines to form a more highly substituted fluorinated olefin. Similarly, when reacting with an acyl fluoride, the fluoroalkyl group of the silane becomes bonded to the carbonyl carbon of the acyl fluoride and a fluorinated ketone is formed. Finally, when reacting with a fluorinated aromatic compound, one of the fluorines bound to the aromatic nucleus is replaced by the fluoroalkyl group of the silane, and a fluoroalkyl substituted aromatic compound is formed.

The fluoroalkylsilanes useful in this process have the formulas:

$$R_3^1Si\text{-}CF_2\text{-}T \text{ and } R_3^1SiC_6F_5$$

wherein:

each $R^1$ is independently selected from hydrocarbyl or hydrocarbyl containing inert substituents; and T is fluorine, or $$\begin{array}{c} W \\ | \\ -C-F \\ | \\ W \end{array}$$

wherein:

each W is independently selected from hydrocarbyl, hydrocarbyl containing inert substituents and/or reactive silyl radicals, hydrogen and fluorine.

The group $-C_6F_5$ represents pentafluorophenyl.

In preferred silicon compounds, each $R^1$ is independently selected from $C_1$-$C_4$ normal alkyl and phenyl, and in especially preferred silicon compounds, each $R^1$ is independently selected from phenyl and methyl, and in the most preferred silicon compounds, $R^1$ is methyl. In one preferred embodiment of the silicon compound, T is fluorine. In another preferred embodiment T is perfluoroalkyl, and in an especially preferred embodiment T is perfluoro normal (straight chain) alkyl. It is also preferred that the fluoroalkylsilane contain no more than two reactive silyl radicals. A preferred compound is $R_3^1SiR^4SiR_3^1$, wherein $R^4$ is perfluoroalkyl. It is also preferred to combine two or more of the above preferred embodiments of the fluoroalkylsilane. It is believed that the present reactions are subject to "steric hindrance", a concept well known to those skilled in the art. Thus, the use of silicon compounds (and other reactants) that are not sterically hindered will usually lead to improved results, such as shorter reaction times.

Silicon compounds useful in this process include, but are not limited to, trimethyl-n-perfluorohexylsilane, phenyldimethylpentafluorophenylsilane, 1,6-bis(trimethylsilyl)perfluorohexane, 1,8-bis(trimethylsilyl)perfluorooctane and 1,10-bis(trimethylsilyl)perfluorodecane.

The fluoroalkylsilanes useful in the present invention may be made by generally following the procedures of A. E. Jukes and H. Gilman, *J. Organometal. Chem.*, Vol. 18, P33-34 (1969) and R. Smith and H. Gilman, *J. Organometal. Chem.*, Vol. 46, 251-254 (1972), both of which are hereby included by reference. Typical procedures are given in Experiments 2 and 3.

The fluorinated olefins used in the present process have the formula:

$$\begin{array}{c} F \quad M \\ | \quad | \\ C=C, \\ | \quad | \\ Q^1 \quad Q^2 \end{array}$$

wherein:

$Q^1$ and $Q^2$ are independently selected from fluorine and $-CFX_2$;

M is selected from $-CFX_2$ and $-OCFX_2$;

each X is independently selected from fluorine, chlorine, hydrogen, hydrocarbyl and hydrocarbyl containing inert substituents and/or reactive vinyl radicals, provided that each X may be such that the groups $Q^1$ and $Q^2$ are part of a carbocyclic or heterocyclic ring which includes the reactive fluorinated olefin.

It is to be understood that any of the olefin structures shown herein are not meant to convey whether the olefin is a cis or trans compound (if applicable), and that both cis and trans isomers are operable in this process.

In preferred olefins, $Q^2$ is fluorine, $Q^1$ is perfluoroalkyl and M is perfluoroalkyl or perfluoroalkoxy. In another preferred embodiment, $Q^1$ and $Q^2$ are fluorine. In another preferred embodiment $Q^1$ and $Q^2$ are fluorine and M is perfluoroalkyl or perfluoroalkoxy. In a most preferred embodiment of the olefin, $Q^2$ is fluorine, $Q^1$ is normal perfluoroalkyl, and M is normal perfluoroalkyl or normal perfluoroalkoxy. In another preferred embodiment, $Q^1$ and $Q^2$ are fluorine and M is normal perfluoroalkyl or normal perfluoroalkoxy. In another preferred embodiment, $Q^1$ and $Q^2$ form a perfluorinated carbocyclic or heterocyclic ring. In a more preferred embodiment, the $Q^1$ and $Q^2$ groups of a carbocylic ring have the formula $-(CF_2)_n-$ wherein n is 2,3, or 4. In fluorinated olefins containing reactive vinyl radicals, it is preferred that there be only one reactive vinyl radical (therefore a total of two reactive olefinic groups in the molecule). It is also preferred to use various combinations of the above preferred embodiments of the fluorinated olefin.

Fluorinated olefins useful in this process include, but are not limited to hexafluoropropylene, perfluorocyclopentene, perfluorocyclobutene, perfluoro(2-phenoxypropyl vinyl ether), perfluoro[bis-1,12-(1-cyclopentenyl)dodecane], perfluoro[bis-1,6-(1-cyclopentenyl)hexane], perfluoro[bis-1,8-(1-cyclopentenyl)octane], and perfluoro[bis-1,10-(1-cyclopentenyl)decane]. The fluorinated olefins useful in this process are available commercially, may be made by procedures known to those skilled in the art or made by methods described herein.

It is to be understood that if there is more than one vinylic fluorine attached to the carbon of a reactive olefinic group, each such fluorine may be reactive in the present process. Thus, a reactive olefinic group may be di- or trifunctional, in and of itself. Those skilled in the art will realize that it may not be possible to control which vinylic fluorine atom in a reactive olefin reacts first. Furthermore, since the vinylic fluorine atoms are replaced sequentially, the remaining vinylic fluorine atoms will become more sterically hindered (supra), and hence probably less reactive. It is possible to control the reaction of reactive olefins containing more than one vinylic fluorine. For example, the fluoroalkylsilane may be added to an excess of the olefin to minimize reaction of a second vinylic fluorine atom on each reactive olefin group. Use of appropriate molar ratios of reactants, and other techniques, are well known to those skilled in the art for controlling such reactions.

These and other features of the reactions of fluorinated olefins are illustrated in the Examples.

The acyl fluorides useful in the present process have the formula:

$$R^2-C(=O)F$$

wherein:

$R^2$ is hydrocarbyl or hydrocarbyl containing inert substituents and/or acyl fluoride radicals. In preferred acyl fluorides, $R^2$ is perfluoroalkyl. In especially preferred acyl fluorides, $R^2$ is normal perfluoroalkyl. In acyl fluorides in which an acyl fluoride radical is present, it is preferred that only one such radical be present (a total of two acyl fluoride groups in the molecule). Acyl fluorides useful in the present process may be purchased or may be made by techniques known to those skilled in the art.

The products of the reactions of acyl fluorides with fluoroalkylsilanes are fluorinated ketones. As reported by Prakash, et al. (supra), and here, ketones react with trifluoromethylsilanes to yield alcohols (after hydrolysis). It is believed very little of the ketone formed by the reaction of an acyl fluoride with a fluoroalkylsilane further reacts because of the much faster rate of reaction of the acyl fluoride. The use of appropriate molar ratios and other techniques well known to those skilled in the art (supra, for fluorinated olefins) will insure production of the desired fluorinated ketones.

Acyl fluorides useful in this process include, but are not limited to, perfluoropropionyl fluoride and substituted perfluoropropionyl fluorides, perfluoro(2-propoxypropionyl fluoride), benzoyl fluoride, terephthaloyl fluoride and substituted terephthaloyl fluorides, succinoyl fluoride, and perfluoroglutaryl fluoride.

Fluorinated aromatic compounds useful in this process have the formula:

YC$_6$F$_5$ and perfluoropyridine wherein:

Y is a nonreactive group with a Hammett sigma constant of about +0.5 or more. By —C$_6$F$_5$ is meant the pentafluorophenyl group.

Hammett sigma constants are known to those skilled in the art, for example see H. H. Jaffe, *Chem. Rev.*, Vol. 53, 222-223 (1953), which is hereby included by reference, for a discussion and compilation of these constants.

Fluorinated aromatic compounds useful in this process can be made by methods known to those skilled in the art, or can be bought. Useful fluorinated aromatic compounds include, but are not limited to perfluorotoluene, pentafluorobenzonitrile, and pentafluoropyridine.

Preferred fluorinated aromatic compounds include those in which Y is —CF$_3$ and —CN.

By the phrase "containing inert substituents" is meant herein substituents that are inert (unreactive) under the process conditions. Suitable inert substituents include, but are not limited to, fluorine (including complete substitution to form perfluorinated groups) and ether (between hydrocarbyl segments).

By the phrase "reactive vinyl radical" is meant herein radicals of the formula:

wherein:

any two of the remaining bonds are independently selected from $Q^1$, $Q^2$ and M, wherein $Q^1$, $Q^2$ and M are as defined above; provided that any carbon atom α to a vinylic carbon has bonded to said α carbon at least one fluorine atom.

It is preferred that the reactive vinyl group be perfluorinated.

By the phrase "reactive silyl radical" is meant herein radicals of the formula:

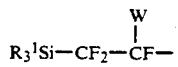

wherein:

$R^1$ and W are as defined above.

By the phrase "acyl fluoride radical" is meant herein the radical —C(=O)F.

When both the fluoroalkylsilane and the other fluoroorganic compound have two reactive (in the present process) groups a polymer is formed. This is an especially preferred combination.

The term perfluoroalkyl group also includes perfluoroalkyl groups with one or more ether linkages in the group, connecting perfluoroalkyl(ene) segments.

Catalysts for the above process include selected catalysts useful in Group Transfer Polymerization (GTP) and sources of fluoride and bifluoride ion. Useful GTP catalysts are found in U.S. Pat. No. 4,588,795, column 5, line 14 to column 7, line 6 (which is hereby included by reference). Such catalysts are described by said U.S. Pat. No. 4,588,795 at col.5, lines 14-18 as "a salt comprising a suitable cation and an oxyanion which can form a conjugate acid having a pKa (DMSO) of about 5 to about 24, preferably 6 to about 21, more preferably 8 to 18. Sources of fluoride and bifluoride ion include, but are not limited to, the alkali metal fluorides and bifluorides and tetraalkylammonium fluorides and bifluorides.

Catalysts useful in the present process include, but are not limited to, cesium fluoride, tris(dimethylamino)sulfonium fluorosiliconates, tris(dimethylamino)sulfonium bifluoride and tris(piperidino)sulfonium benzoate. Procedures for preparing the tris(dimethylamino)sulfonium salts are found in W. B. Farnham et al., *J. Am. Chem. Soc.*, Vol. 109, 476-483 (1987), which is hereby included by reference. The tris(piperidino)sulfonium benzoate is made by a procedure reported by W. J. Brittain, *J. Am. Chem. Soc.*, Vol. 110, 7440-7444 (1988), which is hereby included by reference. The process with fluorinated olefins is conducted at about −50° to about +50° C., preferably about −50° to about +10° C. The process with acyl fluorides and fluorinated aromatic compounds is conducted at about −10° to about 50° C., preferably about 0° to about 30° C. The upper temperature limit is determined chiefly by the stability of the fluoroalkylsilane under the reaction conditions.

A solvent is required for the reaction, and it is preferred that the reactants and catalyst be at least slightly soluble in the solvent. Preferred solvents are ethers, nitriles and fluorinated solvents such as tetrafluorocyclobutane and 1,1,2,2,3,3-hexafluorocyclopentane. Especially preferred solvents are tetrahydrofuran and the glymes [low molecular weight poly(ethylene oxides) capped with alkyl groups]. Solvents, and indeed all reactants, should be substantially free of water and alcohols, since under the reaction conditions these may react with the starting materials.

Reaction times are usually about 0.2 to 2 hours for the fluorinated olefins, and about 2 to 24 hours for the acyl fluorides and fluorinated aromatic compounds. These times may vary widely depending on the reactants, catalyst and solvent. The progress of the reaction may be monitored by any of several means known to those skilled in the art, such as gas chromatography.

Water should be excluded from these reactions, so it is convenient to use inert gases such as nitrogen or argon to blanket the reaction. Atmospheric pressure is usually satisfactory, but it may be necessary to use elevated pressure when one of the reactants, for example hexafluoropropylene, is a gas. Some agitation of the reaction is desirable, for example with a paddle stirrer or by sonication.

The products may be isolated by a variety of methods known to those skilled in the art, for example, by distillation, or in the case of polymers, by precipitation into a nonsolvent.

The following abbreviations are used in the Examples and Experiments:
CI—chemical ionization
EI—electron impact
GC—gas chromatography
glyme—1,2-dimethoxyethane
GPC—gel permeation chromatography
HFPO—hexafluoropropylene oxide
IR—infrared spectroscopy
M—parent molecular ion
Mn—number average molecular weight
MS—mass spectroscopy
m/z—mass/charge
NMR—nuclear magnetic resonance
TAS—tris(dimethylamino)sulfonium
TGA—thermogravimetric analysis
THF—tetrahydrofuran
TPS—tris(piperidino)sulfonium In the following Examples and Experiments fluorine chemical shifts are reported in ppm from $CFCl_3$. Spectra were recorded on a Nicolet NT200 spectrometer at 188.2 MHz. $^1H$ NMR spectra were recorded on a GE QE-300 spectrometer, and chemical shifts are reported relative to tetramethylsilane at 0 ppm. Infrared spectra were recorded on a Perkin-Elmer 983G infrared spectrometer.

Mass spectral data were obtained using VG 7070-HS (with Varian Vista 6000 GC), VG 70-SE (with HP 5790 GC), VG ZAB-2F (high resolution), or VG ZAB-E (low resolution) instruments.

Gas chromatography was done using a Hewlett Packard 5890 instrument with 25 m×0.02 mm HP1 crosslinked methyl silicone capillary column, operating at 60°-250° C. (method 1).

Solvents with minimum water concentrations are preferred for the reactions described herein. Tetrahydrofuran (THF), dimethoxyethane (glyme), and ether were distilled from sodium/benzophenone and red under nitrogen. Other solvents were distilled and stored over activated molecular sieves.

All reactions were carried out in an atomsphere of dry nitrogen, and manipulations of hygroscopic or water sensitive catalysts were done in a Vacuum Atmospheres drybox. Low-boiling fluoroolefins were transferred to gas traps and measured by volume unless described otherwise.

EXPERIMENT 1

Preparation of Perfluoroalkyl Bromides

Perfluoroalkyl bromides used were either commercially available or were made by literature methods (see U.S. Pat. No. 4,731,170).

1,8-Dibromohexadecafluorooctane

A mixture of 1,8-diiodohexadecafluorooctane (used as a mixture with the corresponding $C_{10}$ homolog, $C_8/C_{10}=62/38$) (100 g) and bromine (38 mL) was heated in a Hastelloy-lined bomb at 150° C. for 8 hours. The contents were transferred to an erlenmeyer flask with Freon ® 113, and free halogen was destroyed by the addition of sodium thiosulfate and water. The organic layer was dried and stripped to give 77.5 g of white solid (90% yield). Kugelrohr distillation (25°-40° C., 0.05 mm) removed small amounts of impurities.

EXPERIMENT 2

Perfluorooctyltrimethylsilane

A mixture of perfluorooctyl bromide (43.6 g, 87 mmol) and trimethylsilyl chloride (47.4 g, 0.44 mol) was added over 1.0 h to a stirred suspension of magnesium turnings (3.2 g, 131 mmol, crushed prior to reaction in the dry box) in THF (250 mL) at ca. −40° C. The mixture was stirred for 1.0 h at −40° C. and allowed to warm slowly over 18 h. The mixture was filtered under $N_2$ pressure to remove small amounts of unreacted Mg, and ca. ½ of the solvent was removed under vacuum. THe residue was diluted with pet. ether, filtered through Celite ®, and concentrated. Kugelrohr distillation provided 27.6 g of colorless liquid (b.p. 30° to 50° C. 0.1 mm). Although this material is of sufficient purity for most uses, spinning band distillation (ca. 85° C./15 mm) gave >99.8% purity.

$^1$NMR (THF-$d_8$): 0.20 (s); $^{19}F$ NMR (THF-$d_8$): −80.99 (t, J=9.9 Hz, 3F), −118.45 (m, 2F, $SiCF_2$), −121.6 (unresolved m, 6F), 122.5 (s, 2F), −126.0 (s, 2F), −128.1 (m, 2F).

EXPERIMENT 3

1,8-Bis(trimethylslyl)hexadecafluorooctane

A mixture of 1,8-dibromohexadecafluorooctane (27.3 g) and the corresponding $C_{10}$ derivative (4.4 g) (55.5 mmol) and trimethylsilyl chloride (54.9 g, 0.55 mol) was added to a slurry of magnesium turnings (4.11 g, 69 mmol) in THF (300 mL) over 25 minutes at −35° C. The mixture was stirred for 1.5 hours. The mixture was then allowed to warm slowly to 25° C. over 18 hours. Excess magnesium was removed by $N_2$ pressure filtration, and most of the solvent was removed under reduced pressure. Petroleum ether (50 mL) was added, and the mixture was treated (twice) with 500 ml ice water. The organic layer was dried, stripped and kugelrohr distilled to provide 5.17 g (bp 50°-66° C., 0.05 mm; 55% of 1,8-bis(silyl) derivative, and a higher-boiling fraction, 21.4 g (bp 60°-80° C.; 82% 1,8-bis(silyl) derivative and 13% 1,10-bis(silyl) derivative; overall yield ca. 71%). $^1H$ NMR (THF-$d_8$): 0.30 (s). $^{19}F$ NMR (THF-$d_8$/Freon ® 11): −118.54 (s, 4F, $CF_2Si$), −121.52 (s, 8F), −127.97 (s, 4F). GC analysis of the sample used for NMR showed a 92.4/7.6 ratio of $C_8/C_{10}$ fluorocarbon products.

EXAMPLE 1

Reaction of $C_6F_{13}SiMe_3$ with Benzoyl Fluoride

A solution of benzoyl fluoride (124 mg, 1.0 mmol) and $C_6F_{13}SiMe_3$ (392 mg, 1.0 mmole) in THF-$d_8$ was treated with cesium fluoride (5 mg) and heated for 15 minutes at ca. 60° C. NMR analysis showed nearly complete reaction. The mixture was diluted with ether and stripped to give 0.35 g of residue which was kugelrohr distilled (50° C., 0.1 mm) to afford the major fraction. $^1H$ NMR: 8.07 (d, 2H), 7.75 (m, 1H), 7.58 (m, 2H). $^{19}F$ NMR: −80.92 (t, J=9.9 Hz, 3F), −112.4 (m, 2F), −120.6 (brd s, 4F), −122.4 (m, 2F), −125.8 (m, 2F), consistent with the structure $C_6H_5C(O)C_6F_{13}$. GC/MS showed the major component with highest observed mass of m/z=405, consistent with M-F=$C_{13}H_5OF_{12}$.

EXAMPLE 2

Reaction of $C_6F_{13}SiMe_3$ with $CF_3CF_2CF_2OCF(CF_3)C(O)F$

A slurry of cesium fluoride (75 mg) in THF (15 mL) was treated with $CF_3CF_2CF_2OCF(CF_3)C(O)F$ (1.99 g, 6.0 mmol) and then slowly with $C_6F_{13}SiMe_3$ (2.35 g, 6.0 mmol). After the mildly exothermic reaction subsided, the mixture was stirred for 0.5 hours. The bottom fluorocarbon layer was removed to give 2.92 g of colorless oil which was vacuum transferred (kugelrohr) at ca. 25° C./0.1 mm). IR (neat): 1785 cm$^{-1}$ (C=O) and CF stretch at 1200-1250 cm$^{-1}$. $^{19}$F NMR (Freon® 11): −78.94 and −83.64 (AB pattern, J=155 Hz, 2F), −81.0 (m, 3F), −81.60 (t, J=10.0 Hz, 3F), −82.0 (t, J=7.3 Hz, 3F), −116.4 (unresolved m, 2F), −121.6 (brd s, 4F), −123.1 (unresolved m, 2F), −126.6 (unresolved m, 2F), −130.1 (s, 2F), −137.5 (m, 1F). GC/MS showed a small parent ion with m/z=631.949890 (calcd. for $C_{12}F_{24}O_2$=631.951502); major fragment ion with m/z=346.9709010 (calcd. for $C_7F_{13}O$=346.974154. All spectral properties were consistent with the ketone, $CF_3CF_2CF_2OCF(CF_3)C(O)(C_6F_{13})$.

EXAMPLE 3

Reaction of $C_8F_{17}SiMe_3$ with Benzoyl Fluoride

A mixture of benzoyl fluoride (1.36 g, 11 mmol) and cesium fluoride (30 mg) in glyme (5 mL) at 25° C. was treated slowly with $C_8F_{17}SiMe_3$ (4.92 g, 10 mmol). Most of the addition was carried out at ca. 30° C. After 1.5 hours at ambient temperature, the mixture was diluted with ether, filtered, stripped, and kugelrohr distilled to provide 2.63 g, bp 64°-76° C./0.5 mm. An additional 0.5 g of desired product was obtained from a higher-boiling fraction. IR (neat) featured intense band at 1714 cm$^{-1}$. $^1$H NMR (THF-$d_8$): 8.07 (d, 2H), 7.76 (t, 1H), 7.60 (t, 2H). $^{19}$F NMR: −80.99 (t, J=9.8 Hz, 3F), −112.42 (t, J=12.5, 2F), −120.5 (m, 4F), −121.5 (m, 4F), −122.4 (brd s, 2F), −126.0 (m, 2F), consistent with phenyl perfluorooctyl ketone.

EXAMPLE 4

Reaction of $C_8F_{17}SiMe_3$ with Perfluoropropyionyl Fluoride

A mixture of the TAS fluoride salt of perfluoropropionyl fluoride (150 mg) and glyme (2 mL) was cooled to −20° C. and treated with perfluoropropionyl fluoride (1.2 g, 7.0 mmol). Perfluorooctyltrimethylsilane (4.24 g, 8.6 mmol) was added slowly (0.5 hours), and the reaction mixture was warmed slowly to 0° C. After standing at 25° C. for 18 hours, the lower layer was separated and vacuum transferred to give 3.13 g (80%). $^{19}$F NMR (Freon® 11): −81.57 (t, J=9.9 Hz, 3F), −82.42 (s, 3F), −117.74 (s, 2F), −121.2 and −121.5 (overlapping s, 6F), −122.11 (s, 4F), −123.01 (s, 2F), −126.59 (s, 2F). GC/MS (negative ion) showed a major component with parent ion of m/z=565.963196 (calcd. for $C_{11}F_{22}O$=565.9597855). IR (thin film) featured a band at 1786 cm$^{-1}$ (C=O); large C-F envelope 1250 to 1150 cm$^{-1}$. All spectra were consistent with perfluorinated(ethyl octyl ketone).

EXAMPLE 5

Reaction of $C_8F_{17}SiMe_3$ with $CF_3CF_2CF_2OCF(CF_3)C(O)F$

A sample of $CF_3CF_2CF_2OCF(CF_3)C(O)F$ (2.43 g, 7.32 mmol) was treated with the TAS fluoride salt of this acid fluoride (95 mg) and 0.2 mL of 1,1,2,2-tetrafluorocyclobutane. $C_8F_{17}SiMe_3$ (2.3 g, 4.67 mmol) was added dropwise over 15 minutes, and the temperature was maintained at 23°-26° C. using a cold bath. After 2 hours, GC analysis showed 83% $CF_3CF_2CF_2OCF(CF_3)C(O)C_8F_{17}$ and ca. 9% $C_8F_{16}$ dimers. Distillation of the fluorocarbon layer afforded 1.51 g, bp 30°-32° C. (0.1 mm). GC/MS (negative EI) showed a parent ion with m/z=731.937607 (calcd. for $C_{14}F_{28}O_2$=731.945114) and major fragments at 565.953552 ($C_{11}F_{22}O$) and 446.968063 ($C_9F_{17}O$).

EXAMPLE 6

Reaction of $C_8F_{17}SiMe_3$ with $CF_3CF_2CF_2OCF(CF_3)C(O)F$

A mixture of $CF_3CF_2CF_2OCF(CF_3)C(O)F$ (3.80 g, 11.4 mmol) and the corresponding TAS fluoride salt (95 mg) and glyme (0.1 mL) was cooled at 0° C. in a sonicator well. The sonicator was activated and $C_8F_{17}SiMe_3$ (4.24 g, 8.62 mmol) was added dropwise. Sonication was continued for 0.5 hours at 0° C. and then 0.3 hours at 25° C. Volatiles were vacuum transferred (0.1 mm), and the more volatile portion was removed by aspirator vacuum to provide 5.62 g of colorless liquid (GC purity 88%), 78% yield. Spectroscopic properties are as follows: IR (neat) 1786 cm$^{-1}$ (C=O). $^{19}$F NMR (Freon® 11): −78.97 and −83.65 (AB pattern, J=150 Hz, 2F), −81.05 (s, 3F), −81.60 (t, J=10.1 Hz, 3F), −82.0 (t, J=7.3 Hz, 3F), −116.4 (brd s, 2F), −121.4 (m, 4F), −122.2 (m, 4F), −123.1 (m, 2F), −126.65 (m, 2F), −130.15 (s, 2F), −137.5 (m, 1F), consistent with $C_8F_{17}C(O)CF(CF_3)OCF_2CF_2CF_3$.

EXAMPLE 7

Reaction of $C_6F_{13}SiMe_3$ with Perfluorocyclopentene

Perfluorocyclopentene (2.0 g, 9.4 mmol) and cesium fluoride (50 mg, 0.3 mmol) are added to glyme (10 mL) at −40° C. $C_6F_{13}SiMe_3$ (2.35 g, 6.0 mmol) was added dropwise over ca. 20 minutes. After stirring for 0.75 hours at −30° C., the mixture was warmed to 0° C., and the fluorocarbon layer was removed to give 3.05 g. IR (neat) featured 1715 cm$^{-1}$ (C=C) and other prominent bands at 1413, 986, 1363, 1336, 1317, and C-F envelope 1300-1150 cm$^{-1}$. $^{19}$F NMR (Freon® 11): −80.61 (t, J=9.9 Hz, 3F), −107.0 (m, 2F), −110.4 (m, 3F), −120.5 (d, J=10.7 Hz, 2F), −121.15 (unresolved m, 2F), −121.6 (unresolved m, 2F), −122.15 (m, 2F), −125.7 (m, 2F), −130.65 (s, 2F). GC/MS (negative CI) featured a major component with m/z=511.9673610 (calcd. for $C_{11}F_{20}$=511.968060). All data are in accord with perfluoro(1-hexylcyclopentene). Also observed was the 2/1 adduct, m/z=811.9472500 (calcd. for $C_{17}F_{32}$=811.948896).

EXAMPLE 8

Reaction of $C_8F_{17}SiMe_3$ with Perfluorocyclobutene

A mixture of THF (15 mL) and ium fluoride (40 mg) at −78° C. was treated with perfluorocyclobutene (1.25 mL, 12 mmol) and dropwise with $C_8F_{17}SiMe_3$ (2.95 g, 6.0 mmol). The mixture was stirred at −40° C. for 1.0 hours, 0° C. for 1.0 hours, and then warmed to 25° C. The bottom layer was removed to give 1.82 g of colorless oil which was kugelrohr distilled to afford 0.67 g, bp up to 100° C. (0.1 mm). $^{19}$F NMR (Freon® 11) of the mixture of perfluoro 1-octyl- and 1,2-dioctylcyclobutene: −81.54 (t, J=10 Hz), −95.2 (m), −111.9 (m), −112.0 (m), −113.2 (s), −114.6 (m), −119.5 (m), −121.5 to −122.5 (overlapping m), −123.0 (m), −126.6 (m). GC/MS (negative CI) showed a shorter retention time component with M+ of m/z=561.964844 (calcd. for $C_{12}F_{22}$=561.964866) and a longer retention time component with M+ of m/z=961.9392850 (calcd. for $C_{20}F_{38}$=961.939314), consistent with a mixture of 1/1 and 2/1 adducts.

EXAMPLE 9

Reaction of $C_8F_{17}SiMe_3$ with Hexafluoropropene

A mixture of hexafluoropropene (3.0 g, 20 mmol) and glyme (15 mL) at −50° C. was treated with cesium fluoride (20 mg) and then dropwise with $C_8F_{17}SiMe_3$ (2.46 g, 5.0 mmol). The mixture was allowed to warm slowly (−50° C., 40 minutes; 40° C., 15 minutes; −30° C., 15 minutes; −20° C., 15 minutes) and was stirred at 0° C. for 1 hour. The lower layer was removed and vacuum transferred to provide 3.94 g which was fractionated at 140 mm to give lower-boiling materials and then 1.59 g of colorless oil, bp ca. 102° C. $^{19}$F NMR (Freon® 11): −69.54 (dd, J=6.9, 19.9 Hz. 3F), −81.56 (t, J=10.0 Hz, 3F), −85.25 (minor s), −118.65 (m, 2F), −122.22 (brd s, 6F), −123.05 (brd s, 2F), −123.88 (brd s, 2F), −127.0 (brd s, 2F), −156.5 and −157.9 (AB pattern, J=150 Hz, 2F), −154.9 (minor m for cis isomer), consistent with $CF_3CF=CF(C_8F_{17})$. GC/MS analysis (negative CI) of the higher-boiling fraction from a similar reaction showed five components with M corresponding to 2/1 adducts, e.g., 949.922409, 949.943283, and 949.937134 (calcd. for $C_{19}F_{38}$=949.939314).

EXAMPLE 10

Reaction of Dimethylpentafluorophenylphenylsilane with Perfluoro[(2-phenoxy)propyl vinyl ether]

A mixture of the title silane (1.0 g, 3.3 mmol) and vinyl ether (1.51 g, 3.5 mmol) in THF (5 mL) at −78° C. was treated dropwise with a solution of TAS trimethyldifluorosiliconate (20 mg) in THF (0.5 mL). The solution was allowed to warm to 25° C. and was stirred for 1 hour. GC analysis showed some starting vinyl ether, dimethylphenylfluorosilane, and two major products with longer retention times. GC/MS showed both products to exhibit parent ions of nominal mass 578, observed 577.9611 (calcd. for $C_{17}F_{18}O_2$=577 9610). The next highest fragment observed was 332.9784 (calcd. for $C_9F_{11}O$=332.9773). Also observed was 244.9921 (calcd. for $C_8F_7O$=244.98371). Fragmentation patterns are consistent with products resulting from substitution of vinylic fluorines rather than aryl fluorines. Mass spectral data are consistent with $(C_6F_5O)CF(CF_3)CF_2OCF=CF(C_6F_5)$ isomers.

EXAMPLE 11

Reaction of 1,6-Bis(trimethylsilyl)perfluorohexane with Perfluorocyclopentene

A mixture of perfluorocyclopentene (4.24 g, 20 mmol) and glyme (15 mL) at −40° C. was treated with cesium fluoride (30 mg) and then dropwise with 1,6-bis(trimethylsilyl)perfluorohexane (2.23 g, 5.0 mmol). The mixture was allowed to warm slowly to 0° C. an stirred for 1.0 hours. The fluorocarbon layer was separated (after trituration with glyme at 0° C.) to give 2.59 g of colorless oil. Kugelrohr distillation gave 2.0 g, bp 50° C. (0.1 mm). $^{19}$F NMR (Freon® 11): −107.89 (d, J=6 Hz, 4F), −111.33 (m, 6F), −121.38 (d, J=13 Hz, 4F), −121.98 (brd s) and −122.48 (brd s, combined=8F), −131.54 (s, 4F), consistent with perfluoro[1,6-bis(cyclopent-1-enyl)hexane].

EXAMPLE 12

Reaction of 1,8-Bis(trimethylsilyl)perfluorooctane with Perfluorocyclopentene

A solution of 1,8-bis(trimethylsilyl)perfluorooctane (4.36 g of a 76/24 mixture of $C_8/C_{10}$ compounds, 7.7 mmol) in glyme (5 mL) was added dropwise to a solution of perfluorocyclopentene (6.36 g, 30 mmol) and TPS benzoate (40 mg) in glyme (20 mL) at ca. −30° C. The mixture was warmed slowly to 0° C., stirred for 1.0 hours, then warmed to 25° C. The lower layer was removed and evaporated to give 4.99 g. The solvent was evaporated separately to give an additional 1.0 g of material. Kugelrohr distillation gave 4.61 g of white solid (as a 76/24 mixture). The pot residue consisted mainly of 3/2 adducts and small amounts of higher oligomers. $^{19}$F NMR (Freon® 11): −107.9 (m), −111.35 (brd s), −121.36 and −121.42 (s), −122.0 (s), −131.56 (s), consistent with the assigned product mixture, perfluoro[1,8-bis(cyclopent-1-enyl)octane] and the corresponding $C_{10}$ structure. IR (neat) featured 1717 cm$^{-1}$ (C=C). $^{19}$F NMR of the 3/2 adduct featured $CF_2$ signals for the central ring at −106.9 (allylic) and −135.5. GC/MS showed the major component with M-F of m/z=866.947144 (calcd. for $C_{20}F_{33}$=866.9473063); the minor component exhibited 966.943481 (calcd. for $C_{22}F_{37}$=966.9409191). Higher-boiling components were predominantly the 3/2 adducts: (EI negative ion) showed a parent ion with m/z=1559.917969 (calcd. for $C_{35}F_{60}$=1559.9041932).

EXAMPLE 13

Reaction of 1,6-Bis(trimethylsilyl)perfluorohexane with Perfluorocyclobutene

A solution of perfluorocyclobutene (6.5 g, 40 mmol) in glyme (25 mL) at −40° C. was treated with cesium fluoride (30 mg) and then 1,6-bis(trimethylsilyl)perfluorohexane (2.23 g, 5.0 mmol). The mixture was warmed slowly to 0° C., stirred for 1.0 hour, then warmed to 25° C. Excess perfluorocyclobutene was removed under vacuum to a trap. Evaporation gave 2.66 g which was kugelrohr distilled to provide 1.20 g (bp 25°–36° C./0.1 mm). A higher-boiling fraction (0.43 g, 50°–100° C.) was contaminated with 3/2 adduct. $^{19}$F NMR (THF-d$_8$/Freon® 11): −92.47 (brd s, vinyl CF), −111.48 (brd s, allylic $CF_2$), 114.11 (m, allylic $CF_2$), −118.95 (brd s, allylic $CF_2$), −121.4 (brd s, $CF_2$), −122.49 (brd s, $CF_2$), consistent with the assigned structure, perfluoro[1,6-bis(cyclobut-1-enyl)hexane]. GC/MS showed the correct nominal mass for a $C_{14}F_{22}$ parent ion.

EXAMPLE 14

Reaction of 1,8-Bis(trimethylsilyl)perfluorooctane with Hexafluoropropene

A solution of 1,8-bis(trimethylsilyl)perfluorooctane (3.0 g as an 87/13 mixture of $C_8/C_{10}$ derivatives, 5.38 mmol) and hexafluoropropene (3.3 g, 22 mmol) in glyme (20 mL) at −50° C. was treated with cesium fluoride (20 mg). The mixture was warmed slowly to ca. 20° C. Since reaction seemed to be slow, the mixture was again cooled to −50° C. and treated with another batch of cesium fluoride (25 mg). The mixture was warmed slowly and was stirred for 18 hours. The lower layer was separated, stripped, and kugelrohr distilled to give 0.63 g, bp 30°–70° C./0.1 mm, and 0.77 g of residue. $^{19}$F NMR (Freon® 11, distilled portion): −69.53 (dd, J=7.1, 19.9 Hz, CF$_3$), −118.7 (m, allylic CF$_2$), −122.1 (m, CF$_2$), −123.9 (s, CF$_2$), −156.51 and −157.87 (AB pattern, J=142, vinyl CF). GC/MS (negative EI) showed five components (4 minor and 1 major), parent ion with M of m/z=661.965118 (calcd. for $C_{14}F_{26}$=661.9584837), isomers of perfluorotetradeca-2,12-diene (including some double bond rearrangement isomers). A set of components with longer retention times was also observed: 761.95750 (calcd. for $C_{16}F_{30}$=761.9520966), consistent with the assigned perfluorohexadecadiene isomers.

EXAMPLE 15

One-step Reaction of Perfluorocyclopentene with 1,6-Bis(trimethylsilyl)perfluorohexane A mixture of glyme (5 mL) and perfluorocyclopentene (1.39 g, 6.56 mmol) at −40° C. was treated with cesium fluoride (30 mg) and dropwise with 1,6-bis(trimethylsilyl)perfluorohexane (2.93 g, 6.56 mmol). The mixture was stirred for 0.5 hours at −30° C., 1.0 hours at 0° C., and then warmed to 25° C. A further exothermic reaction occurred. After 1.5 hours, solvent was decanted and the fluorocarbon resin was washed with petroleum ether. The product was dissolved in Freon® 113, filtered and evaporated to give 2.39 g. Kugelrohr distillation gave ca. 1.2 g of volatile material which was predominantly the 1,6-bis(perfluorocyclopent-1-enyl) derivative described in separate Example 11. F NMR (Freon® 11) of the viscous residue showed: −107.1 (brd s, a=13), −108.0 (s, a=3), −111.5 (s, a=17), −118.5 (s, a=14), −121.5 (m, a=3), −122.0 (brd s, a=16), −131.5 (s, a=3), −135.5 (s, a=6), consistent with a chain-extended oligomer containing (on the average) two cyclopentenyl end groups and four internal rings.

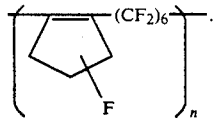

Analysis (poly-HFPO standards) gave Mn ca. 2350, in good agreement with the above NMR analysis.

EXAMPLE 16

Two-step reaction of 1,6-Bis(trimethylsilyl)perfluorohexane and 1,6-Bis(perfluoro-1-cyclopentenyl)perfluorohexane A mixture of the title diene (0.93 g, 1.36 mmol) and bis-silane (0.61 g, 1.36 mmol) was warmed gently to give a homogeneous liquid. Cesium fluoride (25 mg) was added, but no exotherm was observed. A small sample (2 mg) of TAS macrocyclic ether/F complex was added, also with no effect. After 48 hours, 0.2 mL glyme was added, and the temperature rapidly increased to 40° C. After 2 hours, the product was taken up in Freon® 113, stripped, and kugelrohr distilled to remove unreacted diene. Obtained 0.77 g of residue whose $^{19}$F NMR spectrum was the same as that for Mn 2400 oligomer described in Example 15.

EXAMPLE 17

Reaction of 1,6-Bis(trimethylsilyl)perfluorohexane and F(O)CCF(CF$_3$)OCF$_2$CF$_2$OCF(CF$_3$)C(O)F A solution of perfluorinated alkoxide was prepared by adding the symmetric ½ adduct of oxalyl fluoride/hexafluoropropylene oxide (45 mg) to TAS trimethyldifluorosiliconate (27 mg) in ca. 0.2 mL glyme. The resulting solution was added to a sample of the above bis-acid fluoride (2.13 g, 5.0 mmol), and 1,6-bis(trimethylsilyl)perfluorohexane (2.23 g, 5.0 mmol) was added dropwise at 0° C. with sonicator stirring. After warming to room temperature, cesium fluoride (28 mg) was added and the mixture was heated to 40°–45° C. for 1.5 hours. Product was diluted with Freon® 113, filtered, stripped, and subjected to vacuum (60° C.) to remove small amounts of volatile material. There was obtained 2.86 g of residue. IR featured bands at 1785 cm$^{-1}$ (ketone C=O) and 1882 cm$^{-1}$ (acid fluoride C=O). $^{19}$F NMR (Freon® 11): +25.75 (m), −82.3 to −84.0 (m's overlapping singlets at −81.0, −82.5, and −83.0), −86.9 to −88.3 (m), −90 to −92.0 (m), −116.5 brd s), −121.5 (brd s), −131.2 (m), −132.3 (m), −137.2 (m), consistent with an alternating copolymer containing, on the average, 6 repeat units and 2 acid fluoride ends.

EXAMPLE 18

Reaction of Terephthaloyl Fluoride and 1,8-Bis(trimethylsilyl)perfluorooctane

A mixture of terephthaloyl fluoride (0.85 g, 5.0 mmol), cesium fluoride (20 mg) and glyme (4 mL) was treated slowly with 1,8-bis(trimethylsilyl)perfluorooctane (2.80 g, as a 86/14 mixture of C$_8$/C$_{10}$ derivatives, 5.0 mmol). The temperature was controlled between 15° and 26° C. by a cooling bath. After the entire mass had jelled, it was heated to 40° C. for 0.5 hours. Product was filtered and washed several times with petroleum ether and dried in a stream of N2 and then under vacuum to give 3.16 g of insoluble solid. IR (KBr) spectrum featured 1215 cm$^{-1}$ (center of large CF envelope), 1719 cm$^{-1}$ (major ketonic C=O), a small band at 1820 cm$^{-1}$ [ArC(O)F], and an unassigned peak at 1775 cm$^{-1}$. Spectra were consistent with the copolymer, +C(O)C$_6$H$_4$C(O)(CF$_2$)$_8$+, as the product. TGA analysis showed good thermal stability to ca. 290° C., but rather rapid weight loss at higher temperatures.

EXAMPLE 19

Reaction of 1-Trimethylsilylperfluorohexane with Perfluorotoluene

A mixture of perfluorotoluene (1.89 g, 8.0 mmol) and glyme (7 mL) at −20° C. was treated with cesium fluoride and 1-trimethysilylperfluorohexane (1.57 g, 4.0 mmol). The mixture was stirred at −20° C. for 1.0 hours, at 0° C. for 1.0 hour, and then at 25° C. for 18 hours. The upper layer was separated, stripped, and kugelrohr distilled to give 0.63 g. GC analysis showed one major product. GC/MS showed one major product and two minor isomers, each of which exhibited intense parent ions of m/z=536, consistent with the $C_{13}F_{20}$ structures, with para $(C_6F_{13})C_6F_4(CF_3)$ predominating. $^{19}F$ NMR showed signals for perfluorotoluene along with −57.02 (t, J=21.8 Hz), −80.8 (t, $CF_3$), −107.0 (m), −121.7, 122.2, and −122.4 (m's), −126.0 (m), and new aromatic signals at −137.2 (m), and −138.6 (m).

EXAMPLE 20

Reaction of 1-Trimethylsilylperfluorooctane with Perfluorotoluene

A solution of perfluorotoluene (2.83 g, 12 mmol) in glyme (10.5 mL) at −20° C. was treated with cesium fluoride (45 mg) and then slowly with 1-trimethylsilyl-perfluorooctane (2.95 g, 6.0 mmol). The mixture was stirred at −20° C. for 45 minutes, at 0° C. for 2 hours, and at ca. 25° C. for 18 hours. The lower layer was removed to give 1.10 g. The top layer was evaporated and kugelrohr distilled to give 1.62 g of white solid, bp 65° C./0.1 mm. GC analysis of he bottom layer showed three components: 34% monoalkylated product, and two smaller peaks (10% and 19%) ascribed to products of multiple substitution. $^{19}F$ NMR (acetone-$d_6$): −57.06 (t, J=21.9 Hz, 3F), −80.85 (t, J=10 Hz, 3F), −107.2 (m, 2F), −121.4 (brd s), −122.0, and −122.4 (m's), −129.5 (m, 2F), −137.4 (m, 2F), −139.0 (m, 2F), consistent with perfluoro[p-octyltoluene] as the major product.

EXAMPLE 21

Reaction of 1-Trimethylsilylperfluorooctane with Pentafluorobenzonitrile

A solution of pentafluorobenzonitrile (1.16 g, 6.0 mmol) in glyme (6 mL) was treated with cesium fluoride (25 mg) and then dropwise with 1-trimethylsilyl-perfluorooctane (2.46 g, 5.0 mmol). Temperature was controlled below 29° C. by a cooling bath. After stirring for 18 hours, the top layer was stripped and kugelrohr distilled to give 0.33 g starting nitrile and then 0.63 g of white solid, bp 40°-80° C. GC/MS showed the major component with parent ion of m/z=592.9645 (calcd. for $C_{15}F_{21}N$=592.9695) and a minor component also with m/z=592.9685. $^{19}F$ NMR (THF-$d_8$/Freon ® 11): −80.89 (t, J=10.0 Hz, $CF_3$), −105.2 (m) and −106.9 (m, benzylic $CF_2$), −120.8 to −122.3 (series of brd s, $CF_2$), −125.9 (m), −127.5 (m), −131.3 (m), −132.8 (m), −136.9 (m), −143.6 (doubled triplet, Jt=21.5 Hz, Jd=9.4), −145.5 (doubled triplet, Jt=21.5, Jd=9.4 Hz), consistent with the major isomer as para- and the minor isomer as ortho-substituted $(C_8F_{17})C_6F_4CN$. $^{19}F$ NMR of the crude fluorocarbon layer indicated that multiple substitution had also occurred.

The above reaction was repeated under similar conditions except that addition of the silane was carried out at −30° C. and a slow warm-up procedure was used. There was obtained 1.59 g of white solid (54%).

EXAMPLE 22

Reaction of 1-Trimethylsilylperfluorooctane with Perfluoropyridine

A mixture of pentafluoropyridine (1.06 g, 6.25 mmol), cesium fluoride (25 mg) and glyme (7 mL) was treated dropwise with 1-trimethylsilylperfluorooctane (2.46 g, 5.0 mmol) over ca. 40 minutes. The top layer was separated, stripped, and kugelrohr distilled to give 0.94 g, bp 42°-78° C./0.1 mm. The bottom layer (0.80 g) was distilled to give another 0.18 g of mono-substitution product and 0.38 g of multiple substitution products. $^{19}F$ NMR (acetone-$d_6$/Freon ® 11) of the major component: −80.92 (t, J=10.0 Hz, $CF_3$), −89.0 (m, F's ortho to N), −121.4, −121.8, and −122.4 (brd m's, $CF_2$), −125.9 (m), −108.4 (m, $CF_2$ adjacent to ring), −140.2 (m, meta ring F's), consistent with the structures, $(C_8F_{17})C_5F_4N$.

EXAMPLE 23

Reaction of 1,8-Bis(trimethylsilyl)perfluorooctane with Perfluoropyridine

A solution of pentafluoropyridine (5.4 g, 32 mmol) in glyme (15 mL) at 0° C. was treated with cesium fluoride (25 mg) and then dropwise with 1,8-bis(trimethylsilyl)-perfluorooctane (3.0 g, as an 80/20 mixture of $C_8/C_{10}$ derivatives, 5.3 mmol). The mixture was stirred at 0° C. for 1.5 hours, warmed slowly to 25° C., and stirred for 18 hours. Evaporation and fractional kugelrohr distillation gave 0.45 g of lower-boiling materials, 1.99 g, bp 80° to 142° C./0.1 mm, which was predominantly (1.41 g) a white solid. $^{19}F$ NMR: −88.7 (m, F's ortho to N), −108.3 (m, benzylic $CF_2$), −121.3 and −121.9 (s, $CF_2$), −140.0 (m, F's meta to N). The major product was thus the para, para' isomer of $C_5F_4N(CF_2)_8C_5F_4N$. Recrystallization of the solid from (hot) hexane removed small amounts of impurities. $^{19}F$ NMR of the liquid product portion showed this to be a substituted —$(CF_2)_8$— fragment: one end with $C_5F_4N$, the other end with H.

EXPERIMENT 4

Reaction of 1,10-Bis(perfluoro-1-cyclopentenyl)perfluorodecane and $TMSOCH_2CF_2CF_2OCF(CF_3)CF_2OCF(CF_3)CH_2OTMS$ A mixture of the title diene (1.20 g as a 87/13 mixture of 1,10-decane and 1,12-dodecane derivatives, 1.33 mmol) and the above bis(silyl) ether were heated until the solid melted and dissolved. TAS macrocyclic ether/fluoride complex (10 mg) was added. Since reaction seemed slow at room temperature, the mixture was heated to 80°-85° C., resulting in the evolution of $Me_3$-SiF. After 1.5 hours at 85° C., the trimethylsilyl fluoride was removed under a stream of $N_2$. Sample was dissolved in FC-75, filtered, and stripped to give 1.85 g of viscous residue. IR (neat) featured 1676 cm$^{-1}$ (C=C). $^1H$ NMR (THF-$d_8$): 5.23 and 5.10 (m's). $^{19}F$ NMR (THF-$d_8$): −79.5 to −83.8 (series of m's), −105.5 (m), −111.2 (m), −112.9 (m), −120.7 (m), −121.7 (brd s), −123.8 (m), −130.2 (brd s), −134.6 (brd s), −144.9 (brd s), consistent with the 1/1 vinyl ether adducts. Signals for anticipated end-groups were not observed. Spectral properties are in accord with the desired oligomer. GPC analysis (polystyrene standards) showed max Mn ca. 5300. Vapor pressure osmometry in Freon ® 113 gave Mn 11,900.

This experiment illustrates the use of an analog of the products obtained in Examples 11 and 12 as a monomer in a polymerization.

What is claimed is:

1. A process for the production of fluorinated organic compounds comprising contacting one or more substituted silanes of the formula

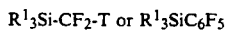

wherein:

each $R^1$ is independently selected from hydrocarbyl or hydrocarbyl containing inert substituents; and T is fluorine, or

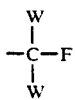

wherein:

each W is independently selected from hydrocarbyl, hydrocarbyl containing inert substituents and/or reactive silane radicals, hydrogen and fluorine, with acyl fluorides, or fluorinated aromatic compounds of the formulas $R^2$—C(=O)F, $YC_6F_5$, or perfluoropyridine, wherein:

$R^2$ is hydrocarbyl or hydrocarbyl containing inert substituents and/or acyl fluoride radicals; and Y is a nonreactive group whose Hammett sigma constant is about +0.5 or more;

in the presence of a suitable catalyst and a solvent.

2. The process of claim 1 wherein $R^1$ is selected from $C_1$-$C_4$ normal alkyl and phenyl.

3. The process of claim 2 wherein $R^1$ is selected from phenyl and methyl.

4. The process of claim 3 wherein $R^1$ is methyl.

5. The process of claim 1 wherein T in the substituted silane is fluorine.

6. The process of claim 1 wherein T in the substituted silane is perfluoroalkyl.

7. The process of claim 1 wherein T in the substituted silane is perfluoro normal alkyl.

8. The process of claim 1 wherein the substituted silane contains no more than two reactive silyl radicals.

9. The process of claim 8 wherein the substituted silane is of the formula $$R_3^1SiR^4SiR_3^1$$

wherein $R^1$ is defined as in claim 1 and $R^4$ is perfluoroalkylene.

10. The process of claim 1 wherein the substituted silanes used are a mixture of two or more fluoroalkylsilanes selected from embodiments wherein T is selected from fluorine, perfluoroalkyl or perfluoro normal alkyl.

11. The process of claim 1 wherein the substituted silane is selected from trimethyl-n-perfluorohexylsilane, phenyldimethylpentafluorophenylsilane, 1,6-bis(trimethylsilyl)perfluorohexane, 1,8-bis(trimethylsilyl)perfluorooctane and 1,10-bis(trimethylsilyl)perfluorodecane.

12. The process of claim 1 wherein a fluoroalkylsilane is contacted with an acyl fluoride of the formula $R^2$—C(=O)F wherein $R^2$ is perfluoroalkyl.

13. The process of claim 12 wherein $R^2$ is normal perfluoroalkyl.

14. The process of claim 1 wherein a fluoroalkylsilane is contacted with an acyl fluoride having a total of two acyl fluoride groups in the molecule.

15. The process of claim 1 wherein a fluoroalkyl silane is contacted with an acyl fluoride selected from perfluoro(2-propoxypropionyl fluoride), benzoyl fluoride, terephthaloly fluoride, substituted terephthaloyl fluorides, succinoly fluoride, and perfluoroglutaryl fluoride.

16. The process of claim 1 wherein the fluoroalkylsilane is contacted with a fluorinated aromatic compound of the formula $YC_6F_5$ where Y is a nonreactive groups having a Hammett sigma constant of about +0.5 or more.

17. The process of claim 16 wherein the fluorinated aromatic compound is selected from perfluorotoluene, pentafluorobenzonitrile and hexafluorobenzene.

18. The process of claim 16 wherein Y is selected from —$CF_3$ and —CN.

19. Process of claim 1 wherein the catalyst for the reaction is selected from (a) a salt comprising a suitable cation and an oxyanion, that are inert under polymerizing conditions, which can form a conjugate acid having a pKa (DMSO) of about 5 to about 24 and (b) sources of fluoride and bifluoride ions.

20. The process of claim 19 wherein the catalyst is a source of fluoride or bifluoride ions selected from the alkali metal fluorides and bifluorides and the tetraalkylammonium fluorides and bifluorides.

21. The process of claim 1 wherein the catalyst is selected from cesium fluoride, tris(dimethylamino)sulfonium fluorosiliconates, tris(dimethylamino)sulfonium bifluoride and tris(piperidino)sulfonium benzoate.

22. The process of claim 1 wherein a fluorinated olefin is used in the process conducted at about −50° C. to about 50° C.

23. The process of claim 22 conducted at about −50° C. to about 10° C.

24. The process of claim 1 wherein an acyl fluoride or fluorinated aromatic compound is used in the process conducted at about −10° C. to about 50° C.

25. The process of claim 24 wherein the process is conducted at about 0° C. to 30° C.

26. The process of claim 1 wherein the reactants and catalyst are at least slightly soluble in the solvent.

27. The process of claim 26 wherein the solvent is selected from ethers, nitriles and fluorinated solvents.

28. The process of claim 27 wherein the solvent is selected from tetrahydrofuran and the glymes.

29. The process of claim 1 conducted in the substantial absence of water.

30. The process of claim 1 wherein the reaction is conducted at pressure above atmospheric pressure.

31. The process of claim 1 wherein the substituted silane and the other fluoroorganic group participating in the reaction both have two reactive groups.

* * * * *